United States Patent [19]

Griep et al.

[11] Patent Number: 5,320,599
[45] Date of Patent: Jun. 14, 1994

[54] DRAINAGE CATHETER

[75] Inventors: Wilhelmus A. M. Griep, Roden; Cornelis P. Nap, Zevenhuizen, both of Netherlands

[73] Assignee: Cordis Corporation, Miami Lakes, Fla.

[21] Appl. No.: 894,174

[22] Filed: Jun. 9, 1992

Related U.S. Application Data

[63] Continuation of Ser. No. 654,061, Feb. 11, 1991, abandoned.

[30] Foreign Application Priority Data

Feb. 14, 1990 [NL] Netherlands .......................... 9000356

[51] Int. Cl.⁵ .............................................. A61B 17/22
[52] U.S. Cl. ...................................... 604/35; 604/43; 604/264; 606/159
[58] Field of Search .................. 604/35, 38, 43–45, 604/264, 266, 267, 269, 280; 128/658; 606/159, 170

[56] References Cited

U.S. PATENT DOCUMENTS

| | | |
|---|---|---|
| 1,902,418 | 3/1933 | Pilgrim . |
| 2,147,652 | 2/1939 | Kennison . |
| 2,804,075 | 8/1957 | Borden ................................ 604/269 |
| 3,429,313 | 2/1969 | Romanelli . |
| 3,542,031 | 11/1970 | Taylor ................................ 604/269 |
| 3,636,940 | 1/1972 | Gravlee ................................ 604/38 |
| 3,955,573 | 5/1976 | Hansen et al. . |
| 4,014,333 | 3/1977 | McIntyre . |
| 4,227,533 | 10/1980 | Godfrey ............................... 604/266 |
| 4,294,251 | 10/1981 | Greenwald et al. . |
| 4,445,892 | 5/1984 | Hussein et al. ....................... 604/101 |
| 4,468,216 | 8/1984 | Muto . |
| 4,610,662 | 9/1986 | Weikl et al. .......................... 604/101 |
| 4,690,672 | 9/1987 | Veltrup ................................ 604/43 |
| 4,715,848 | 12/1987 | Beroza ................................ 604/43 |
| 4,729,763 | 3/1988 | Henrie ................................ 606/159 |
| 4,735,620 | 4/1988 | Ruiz . |
| 4,747,821 | 5/1988 | Kensey et al. . |
| 4,749,376 | 6/1988 | Kensey et al. . |
| 4,755,175 | 7/1988 | Nilsson .............................. 604/280 |
| 4,772,260 | 9/1988 | Heyden ................................ 604/269 |
| 4,795,438 | 1/1989 | Kensey et al. . |
| 4,913,698 | 4/1990 | Ito et al. .............................. 604/43 |
| 4,950,238 | 8/1990 | Sullivan . |
| 4,968,307 | 11/1990 | Dake et al. . |
| 5,037,432 | 8/1991 | Molinari ............................. 606/131 |
| 5,084,013 | 1/1992 | Takase . |
| 5,135,482 | 8/1992 | Neracher ............................ 606/159 |
| 5,135,484 | 8/1992 | Wright ................................ 606/159 |

FOREIGN PATENT DOCUMENTS

| | | |
|---|---|---|
| 0175096 | 7/1985 | European Pat. Off. . |
| 232678 | 8/1987 | European Pat. Off. ............. 606/159 |
| 0485133A1 | 5/1992 | European Pat. Off. . |
| 3019115 | 12/1981 | Fed. Rep. of Germany ...... 606/159 |
| 3421390 | 12/1985 | Fed. Rep. of Germany ...... 606/159 |
| 9005493 | 5/1990 | PCT Int'l Appl. ................. 604/902 |

Primary Examiner—Ralph Lewis
Attorney, Agent, or Firm—Gerstman, Ellis & McMillin

[57] ABSTRACT

A drainage catheter comprises a tubular basic catheter body defining separate catheter lumens respectively comprising a pressure channel and a discharge channel. Connectors are provided at the proximal end of the catheter for respectively connecting the pressure channel to a source of liquid under pressure and the discharge channel to a discharge receptacle. An inlet opening is positioned in the side of the catheter adjacent the distal end thereof. The discharge channel communicates with the inlet opening, while the pressure channel extends from the proximal and distally forward of the inlet opening and then curves rearwardly to join the discharge channel at the inlet opening. In one embodiment of this invention the pressure channel defines a distal portion that is of rigid and fixed dimension to define a spray nozzle of precise, unchanging dimensions. Also, relatively narrow forward and/or side ports are provided between the pressure channel and the exterior to bathe the distal catheter end in x-ray contrast fluid, for example. Likewise, a syringe or the like may be connected to the proximal discharge channel end.

18 Claims, 3 Drawing Sheets

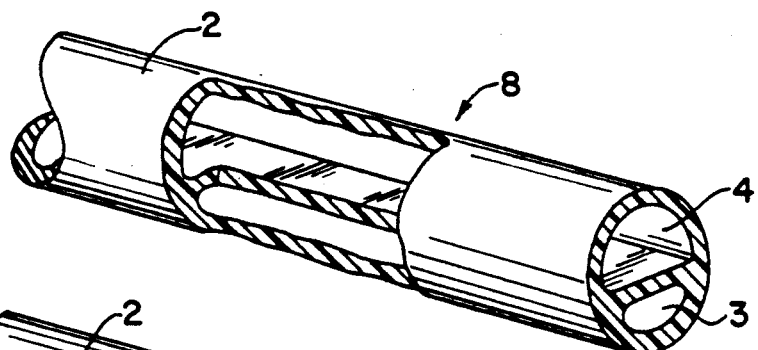
Fig. 2
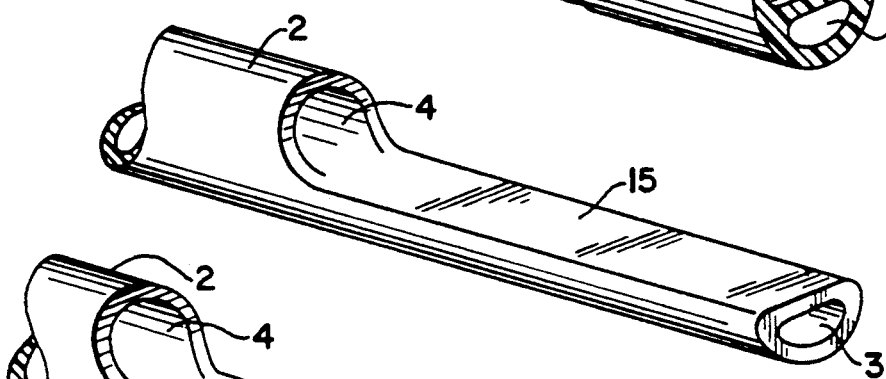
Fig. 3
Fig. 4
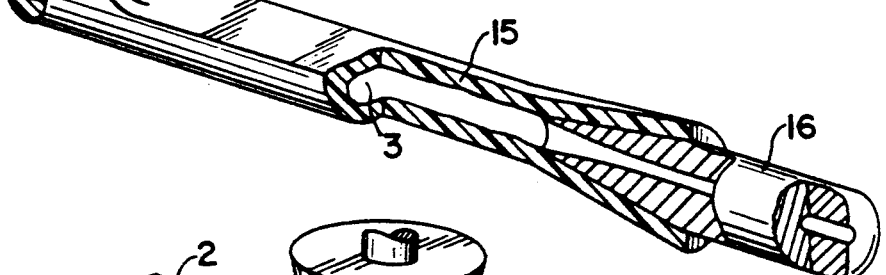
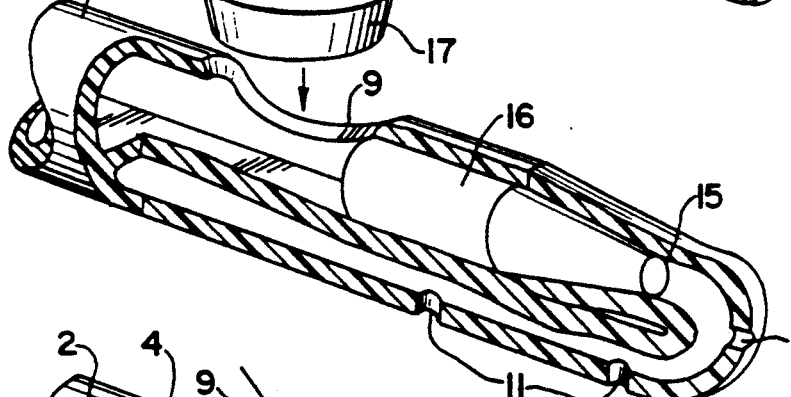
Fig. 5
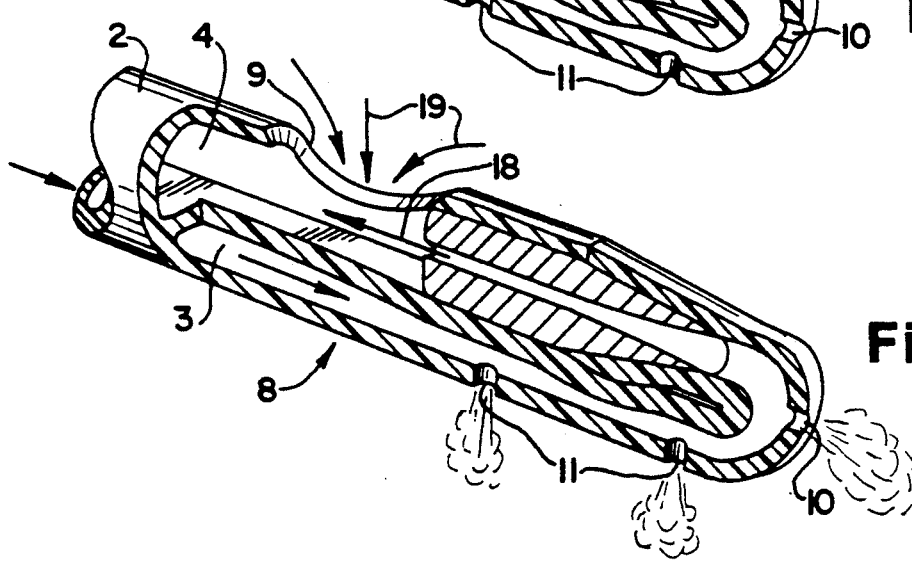
Fig. 6

DRAINAGE CATHETER

CROSS REFERENCE TO RELATED APPLICATION

This application is a Continuation of application Ser. No. 07/654,062, filed Feb. 11, 1991, now Abandoned.

BACKGROUND OF THE INVENTION

The invention relates to a drainage catheter comprising a tube-like basic catheter body with a mutually separated pressure channel or lumen and a discharge channel or lumen. The catheter has connecting means at a rear or proximal end for connecting the pressure channel and the discharge channel to, respectively, a source of liquid under pressure and discharge means such as a container, and may be used for angioplasty or for removing clots, placque and other debris from the body.

Such a drainage catheter is known from the European patent specification 0 175 096. In this known catheter the pressure channel extends distally in the form of a tongue at the front end of the catheter, then curving back again to the discharge channel. A spray nozzle is formed in this tongue, and can deliver a liquid jet through the distal end of the discharge channel. For removing liquids and/or solid particles, the discharge channel is connected to a suction pump. The liquid jet delivered by the spray nozzle is used for the breaking up or crushing of solid particles, for removing the solid particles or deposits from the body vessels of a patient.

The present invention has for its object a suction drainage catheter of the type described which is simpler to use, can be introduced into blood vessels without damaging the vascular system, and is of lower manufacturing cost. Specifically, the catheter of this invention may often be used without a suction pump, with the catheter providing adequate suction of its own.

DESCRIPTION OF THE INVENTION

By this invention, a drainage catheter is provided which comprises a tube-like basic catheter body, with a pair of separate lumens defined within the basic body to form a mutually separate pressure channel and a discharge channel extending the length of the catheter. Connecting means are provided at the proximal end of the catheter for connecting the pressure channel and the discharge channel to, respectively, a source of pressurized liquid and to discharge means.

At the distal end of the catheter, the discharge channel defines an inlet opening which is formed in a side wall of the basic catheter body to communicate with the exterior. The pressure channel is also defined within the basic body to extend forwardly toward the distal end beyond the inlet opening, and then to reversely bend approximately 180 degrees, to extend again a short distance rearwardly. Spray nozzle means is provided to direct a liquid jet from the pressure channel to the discharge channel adjacent the inlet opening, to cause a suction to be created through the inlet opening by aspiration or ejector action. Thus, suction occurs at the location of the inlet opening. Preferably, the spray nozzle is constricted relative to the rest of the pressure channel and is positioned essentially upstream from said inlet opening.

A source of liquid under pressure can thus suffice for the operation of the catheter, so that suction pump is generally superfluous. Only with very long and thin catheters might a suction device still be used to augment the suction due to the aspiration action. During use, the feed of the liquid under pressure may be controlled as to pressure and/or flow rate, with the suction generated being directly dependent on this feed. With the catheter according to the invention, liquids, soft deposits, and solid particles of a size permitting passage through the inlet opening can be removed from the body.

Preferably, in the catheter of this invention there is formed adjacent the distal end at least one narrow passage opening in an outer wall portion of the basic body on a side remote from the inlet opening, and communicating between the pressure channel and the exterior. Thus, during use, a small quantity of fluid under pressure from the pressure channel will pass into the vicinity of the front end of the catheter via the narrow passage opening or preferably openings. When an x-ray contrast fluid is used, the area around the front end of the catheter can thus be made visible on an x-ray screen.

Preferably, a narrow passage opening is also formed in the distal end face of the catheter between the pressure channel and the exterior. Such a narrow passage opening in the leading end face of the catheter can cause contrast liquid to flow out forwardly from the catheter, whereby guiding of the catheter is facilitated as the region forward of the catheter is made visible on an x-ray screen.

Preferably, the catheter carries adjacent its distal end a rigid J or U-shaped tube which is sealingly positioned with at least one leg of the U-shaped tube in the pressure channel, and with a second leg thereof communicating with the discharge channel. The end of the second leg of the U-shaped tube is positioned adjacent to and preferably generally upstream of the inlet opening. Thus, the U-shaped channel defines the reverse bending portion of the flow path described above and also the nozzle, where the discharge channel and the pressure channel meet adjacent the distal end. Thus, the cross-sectional shape of the pressure channel in the reversely bending portion and the nozzle may in this way be very precisely controlled and dimensioned, such that the flow of the liquid under pressure out of the pressure channel and past the inlet opening can create the precisely desired aspiration or ejector action with great reliability. Typically the U-shaped tube is made of a metal such as stainless steel.

Preferably, the second leg of the U-shaped tube is narrowed toward its free end, positioned adjacent the inlet opening, so as to form a jet nozzle for creation of effective suction pressure by the aspiration effect as rapidly moving pressurized fluid passes across the inlet opening and down the discharge channel. Even with catheters having a very small diameter, a reliable suction action by aspiration can be obtained in this way.

As indicated before, the catheter according to the invention can be used with x-ray contrast fluid as the liquid under pressure. In this circumstance, as well as other circumstances, it is preferable for the pressure channel to be connected at its proximal end to a pressurized source of liquid, while the discharge channel is connected at its proximal end to preferably a syringe, or another receptacle for waste fluid received from the discharge channel. A syringe or similar expansible chamber connecting to the discharge channel can be used to block the discharge flow through the discharge channel by holding stationary the syringe plunger, thus preventing fluid flow into the syringe. When in that condition, the x-ray contrast fluid must necessarily flow out of the inlet opening, in that way making visible the surroundings of the front end of the catheter on an x-ray screen. In this condition, the catheter can be maneuvered into the right position, for example near a placque deposit in the body to be removed. Subsequently the plunger of the syringe can be released or pulled back, so that room in the syringe is created for taking up fluid and matter that is sucked into the discharge channel. By suitable manipulating the plunger of the syringe, the suction through the inlet opening can also be increased or decreased, with the suction being primarily from aspiration effects.

The invention is further elucidated in the following description with reference to the annexed figures of embodiments thereof.

DESCRIPTION OF DRAWINGS

FIGS. 2-5 show a partly broken away perspective view of the front end of an embodiment of the catheter at different stages of manufacture;

FIG. 6 shows the front end of the catheter made in FIGS. 2-5 in partly broken away, perspective view in the position of use;

DESCRIPTION OF SPECIFIC EMBODIMENTS

Figure 1:
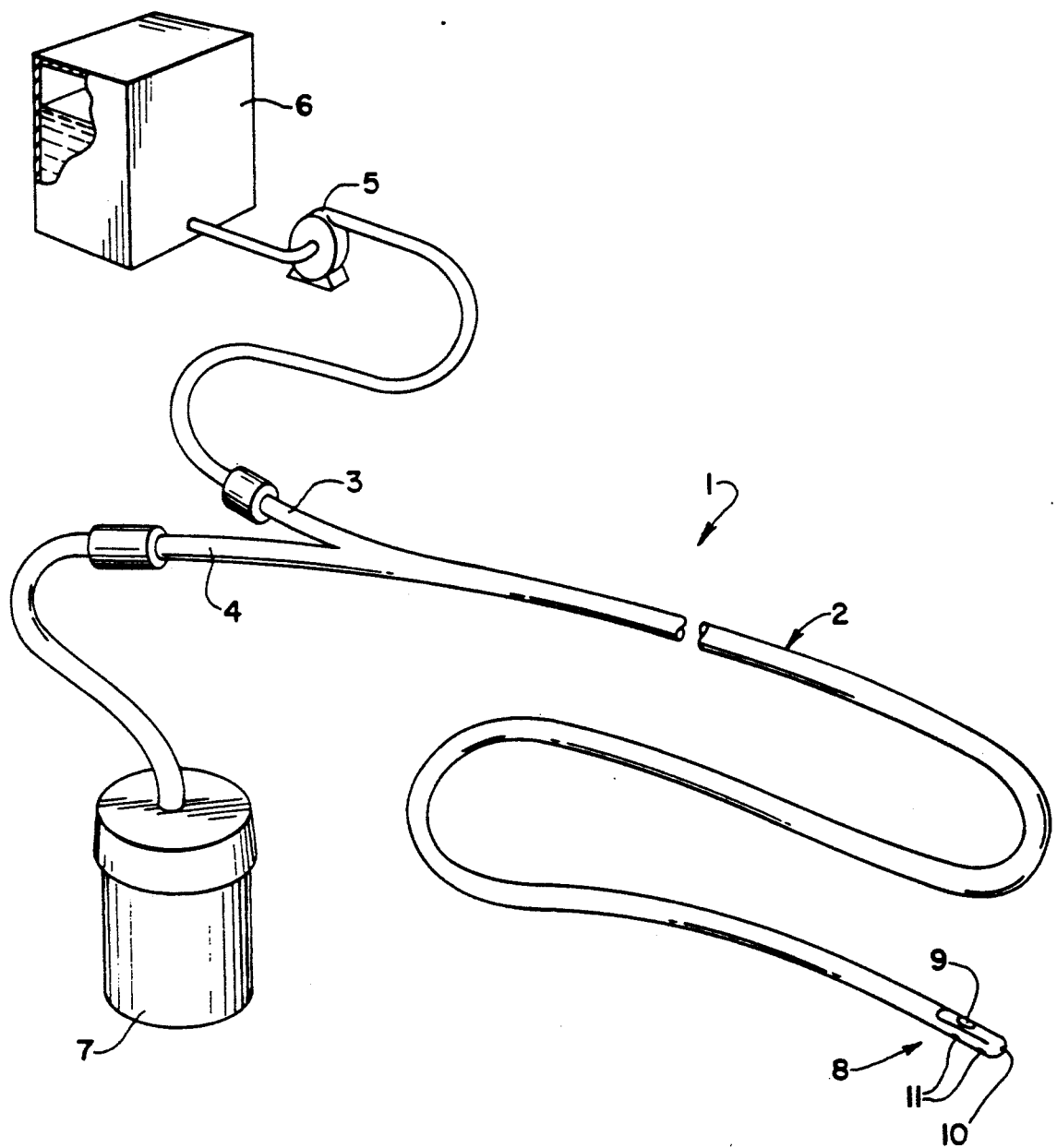
FIG. 1 shows schematically an embodiment of a drainage catheter according to the invention in the position of use.

The drainage catheter 1 shown in FIGS. 1 and 6 comprises a tube-like basic catheter body 2 joined to proximal, mutually separated, branching catheter portions defining pressure channel 3 and discharge channel 4, each of which connect to separate lumens in basic catheter body 2.

Pressure channel 3 in the situation of use is conventionally connected to a source of liquid under pressure, which is indicated in FIG. 1 by a pump 5 which feeds liquid from a reservoir 6.

The discharge channel 4 is conventionally connected to a discharge reservoir 7 wherein substances discharged through the catheter are stored.

There is formed in the side wall of basic catheter body 2 at the front or distal end 8 of catheter 1 an inlet opening 9 (FIG. 6) whereby placque or other material can be drawn into catheter 1 in a manner to be described later. The front end 8 is also provided with narrow leakage openings 10,11 for contrast liquid, which will also be further described later.

FIGS. 2-5 show schematically the manner in which the front or distal catheter end of the present embodiment can be manufactured.

As shown in FIG. 2, tube-like basic body 2 has therein a pressure channel 3 and a discharge channel 4, which are lumens communicating with the previously described branching catheter portions to form extensions of the pressure channel 3 and discharge channel 4 defined therein. Pressure channel 3 of distal tip 8 typically has a smaller diameter than the discharge channel 4. Basic catheter body 2 can for example be manufactured by extrusion.

From a long piece of extruded basic catheter material, as in FIG. 2, a suitable length is removed, and at the rear or proximal end the separate connecting means for the pressure channel and discharge channel 3 and 4 respectively are attached in a usual manner by a sealing process.

The outer wall portion which bounds the discharge channel 4 is ground away from the front end 8 of the basic material so that tube-like pressure channel end 15 remains, as shown in FIG. 3. In this pressure channel end there is fixed a jet nozzle 16, for example by gluing or ultrasonic welding, as in FIG. 4.

The pressure channel end 15 is subsequently bent reversely, and the nozzle 16 inserted into the front end of discharge channel 4 as shown in FIG. 5. The parts are secured into place by, for example, gluing or ultrasonic welding. The various material transitions such as sharp edges are finished smoothly in the usual manner by grinding.

Also as is shown in FIG. 5, an inlet opening 9 is then formed in the side wall of the basic catheter body 2, for example by cutting it therein using a cutter 17.

During use of the catheter, a liquid jet is directed along the inlet opening 9, as indicated in FIG. 6 by the arrow 18, into the discharge channel 4. Through the venturi or aspiration action occurring therein, there results a suction at opening 9 whereby liquids, blood clots, and small, solid particles can be sucked up. This suction is schematically indicated with the arrow 19.

Close to the catheter distal or front end 8, a number of narrow leakage openings 10, 11 are arranged on the side remote from the inlet opening 9 in the outer wall of the basic body bounding the pressure channel 3, and also at the distal end thereof. These leakage openings allow a small quantity of the liquid fed via the pressure channel 3 to escape. During use of the catheter, a contrast fluid may be used as liquid so that the liquid escaping via the openings 10, 11 makes the vicinity of the front end of the catheter visible on an x-ray screen. The leakage opening 10 in the leading distal end face of the catheter delivers liquid forwardly of the catheter, so that the area towards which the catheter is moving is made properly visible on an x-ray screen.

The suction effect through inlet opening 9 is dependent on the fluid velocity and flow rate provided by liquid jet 18. When there is a danger of the discharge channel becoming blocked, a back-pressure spontaneously occurs in the discharge channel at the position of the inlet opening 9, which immediately reduces the suction action. A self-regulating effect of the suction action is thus automatically achieved.

Thus, the catheter of this invention may be used to remove undesired particulate matter and the like from the human body, for example blood clots, loosened fatty tissues, and the like, while the catheter may be advanced through the body with the visualization being aided by its emission of x-ray contrast fluid through apertures connecting with the pressure channel 3.

Figure 7:
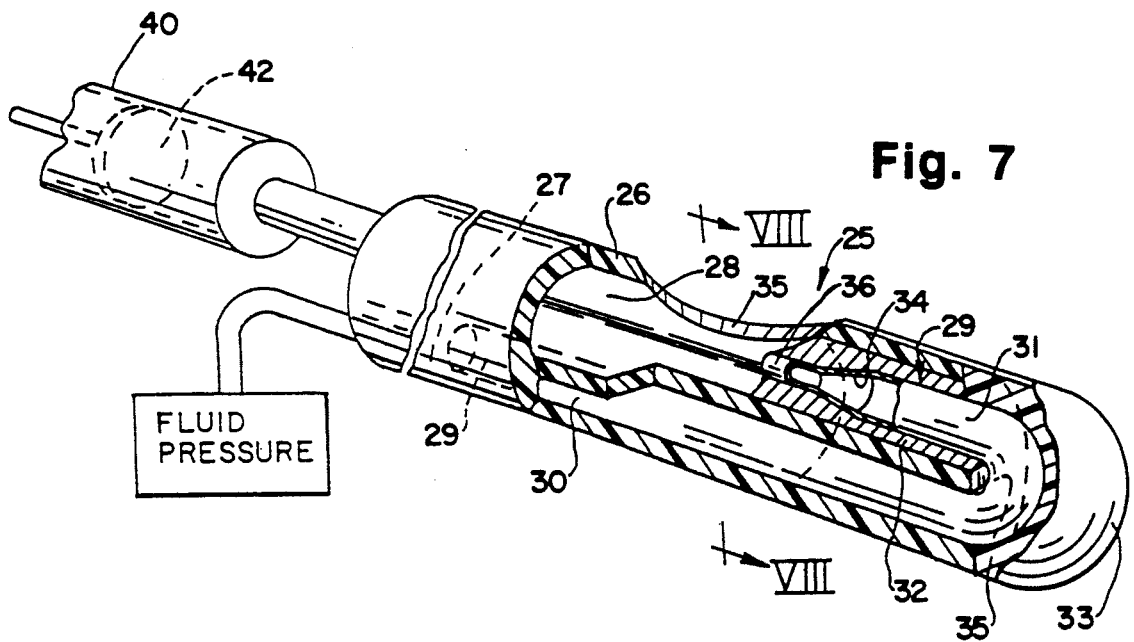
FIG. 7 shows the front end of another embodiment of the catheter according to the invention, in a view corresponding to that of FIG. 6.
Figure 8:
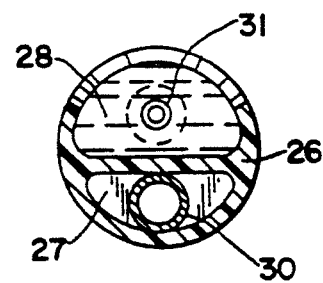
FIG. 8 shows a cross-section according to line VIII—VIII in FIG. 7.

Referring to another embodiment, the catheter 25 as shown in FIGS. 7 and 8 also comprises a basic catheter body 26 defining a pressure channel 27 and a discharge channel 28, having functions similar to channels of the previous embodiment. A J or U-shaped metal tube 29 is arranged with its legs 30, 31 in the pressure channel 27 with the outer end of leg 31 facing discharge channel 28. The U-tube 29 is fixed in its place by hardened filling material or sealant 32. The outer distal end of the catheter may be finished by applying a nose portion 33 of soft plastic material. Such an end portion is in the usual manner ground to a smooth surface.

The leg 31 of the U-shaped metal tube is provided with a narrowed, tapered end portion 34, so that a jet nozzle 36 is formed at the outer end of leg 31. This jet nozzle 36 directs the fluid which is supplied through pressure channel 27 from source 27a in an accurately controlled manner across the interior of inlet opening 35, so that the desired suction aspiration action is obtained in a reliable and efficient way.

Instead of introducing contrast fluid by means of separate openings such as openings 10, 11 in FIGS. 1 and 6, the discharge of contrast fluid at the end of the present embodiment may be controlled by controlling the flow through the discharge channel 28. If flow through the discharge channel is blocked, the flow of fluid supplied through pressure channel 30 will pass through inlet opening 35 outwardly.

The controlled blocking of the discharge channel can be achieved in a very convenient and controllable way by connecting a syringe 40 to the proximal connecting means of the discharge channel. If the plunger 42 of syringe 40 is pulled back, the suction action and discharge of material through the discharge channel can take place in the usual way. By stopping the plunger movement, the suction and discharge is also stopped, and the supplied contrast fluid then flows outwardly through the inlet opening 35, so that the vicinity of the end of the catheter becomes clearly visible to x-ray. Thus, the catheter can alternatively exert suction, or emit x-ray contrast or other media, through inlet opening 35, as controlled by plunger 42 of syringe 40.

The invention is of course not limited to the specific embodiments shown. Instead of manufacturing the front end of the catheter in the manner described starting with the basic body, it is also possible to manufacture a catheter front end separately, for example by injection molding, and to connect this later to the basic body. These and other possible embodiments are considered to fall within the scope of the claims below. The above has been offered for illustrative purposes only, and is not intended to limit the scope of the invention of this application, which is as defined in the claims below.

That which is claimed is:

1. A drainage catheter which comprises a flexible, tubular basic catheter body defining separate catheter lumens respectively comprising a pressure channel and a discharge channel; connector means at a proximal end of said catheter for respectively connecting the pressure channel to a source of liquid under pressure and the discharge channel to discharge means; and inlet opening positioned in the side of said catheter adjacent the distal end thereof, said discharge channel communicating with said inlet opening, said pressure channel extending from said proximal end distally forward of said inlet opening and then curving rearwardly to join said discharge channel at said inlet opening, said pressure channel defining a spray nozzle to direct pressurized fluid in the pressure channel across said inlet opening and into said discharge channel to create a suction adjacent said inlet opening, said spray nozzle being narrowed at one end to form a jet, said one end being positioned to point across said inlet opening and into said discharge channel, and at least one narrow passage opening defined on a side remote from said inlet opening and adjacent said distal end in an outer wall portion of said catheter between said pressure channel and the exterior.

2. The catheter according to claim 1 in combination with said discharge means, in which said discharge means is connected to said discharge channel and in which said discharge means defines expansible chamber means.

3. The drainage catheter of claim 1 in combination with said discharge means wherein said discharge means defines a syringe.

4. A drainage catheter which comprises a tubular basic catheter body defining separate catheter lumens respectively comprising a pressure channel and a discharge channel; connector means at a proximal end of said catheter for respectively connecting the pressure channel to a source of liquid under pressure and the discharge channel to discharge means; an inlet opening positioned in the side of said catheter adjacent the distal end thereof, said discharge channel communicating with said inlet opening, said pressure channel extending from said proximal end distally forward of said inlet opening and then curving rearwardly to join said discharge channel at said inlet opening to direct pressurized fluid from said pressurized channel across said inlet opening and into said discharge channel to create a suction adjacent said inlet opening; and at least one relatively narrow passage opening positioned adjacent said distal end on a side remote from said inlet opening in an outer wall portion of said catheter between said pressure channel and the exterior.

5. The catheter of claim 4 in which said at least one narrow passage opening is formed in the distal end of said catheter between said pressure channel and the exterior.

6. The catheter of claim 4 in combination with said discharge means, in which said discharge means comprises means for immediately varying the pressure in said discharge channel, at the discretion of the user, to block discharge flow through the discharge channel and to alternatively permit said discharge flow through the discharge channel.

7. A drainage catheter which comprises a tubular basic catheter body defining separate catheter lumens respectively comprising a pressure channel and a discharge channel; connector means at a proximal end of said catheter for connecting the pressure channel to a source of liquid under pressure; an inlet opening positioned in the side of said catheter adjacent the distal end thereof, said discharge channel communicating with said inlet opening, said pressure channel extending from said proximal end distally forward of said inlet opening, and curving rearwardly to face said discharge channel at said inlet opening, and defining a proximally facing jet nozzle positioned to direct pressurized fluid from the pressure channel across said inlet opening and into said discharge channel to create a suction adjacent to said inlet opening, said discharge channel at said proximal end being connected to controllably expansible chamber means, whereby expansion of said chamber means permits said suction to be created adjacent the inlet opening, while prevention of expansion of said chamber means prevents said suction so that said pressurized fluid migrates outwardly through said inlet opening, in which, adjacent said distal end, at least one relatively narrow passage opening is defined on a side remote from said inlet opening in an outer wall portion of said catheter between said pressure channel and the exterior.

8. The catheter of claim 7 in which said expansible chamber means is a syringe.

9. The catheter of claim 8 in which said pressure channel is filled with pressurized x-ray contrast fluid.

10. The catheter of claim 7 in which said at least relatively narrow passage opening is formed in the distal end of said catheter between said pressure channel and the exterior.

11. The method of removing unwanted materials from blood vessels, which comprises: introducing a catheter into a blood vessel and advancing said catheter to bring a distally positioned side opening of said catheter adjacent said unwanted materials; passing aqueous liquid through and out of said catheter into contact with said unwanted materials; inducing a reduced pressure through said side opening by passing a jet of said aqueous liquid positioned within said catheter adjacent said side opening, to draw said aqueous liquid outside of said catheter and unwanted materials through said side opening into said catheter, and conveying said drawn aqueous liquid and unwanted materials proximally through a discharge channel defined in said catheter for removal from the body, and further providing intermittent, alternating reduced and elevated pressure to the discharge channel to alternatingly cause said liquid to flow inwardly and outwardly through said opening.

12. The method of claim 11 in which said jet of liquid is proximally directed substantially axially with said catheter.

13. The method of claim 12 in which at least some of said aqueous liquid is passed out of said catheter as a pressurized stream through opening means in the catheter other than said discharge channel.

14. The method of claim 11 in which said aqueous liquid is x-ray contrast media.

15. A method of operating a catheter which comprises a tubular, basic catheter body having a pair of separate lumens defining a pressure channel and a discharge channel, and having an inlet opening positioned adjacent the distal end of said catheter, which inlet opening communicates with said discharge channel, said pressure channel extending distally of said inlet opening and curving rearwardly again to define a spray nozzle positioned adjacent said inlet opening to direct fluids from said pressure channel across said inlet opening into said discharge channel, comprising the steps of: inserting said catheter into the body of a patient; applying pressurized fluid to said pressure channel to cause pressurized fluid to pass through said spray nozzle across said inlet opening and into said discharge channel; and operating means for immediately varying the pressure in said discharge channel to block discharge flow through the discharge channel and to alternatively permit said discharge flow through the discharge channel, to provide, at the discretion of the user, alternating suction to cause debris to be sucked into the catheter through said inlet opening, and other conditions to cause fluid from said pressure channel to pass outwardly through said inlet opening into tissues external to said distal catheter end.

16. The method of claim 15 in which said fluid in the pressure channel is x-ray contrast media.

17. The method of removing unwanted blood vessel debris from the body, which comprises: introducing a catheter into a blood vessel and advancing said catheter to bring a distally positioned side opening of said catheter adjacent to said debris; sequentially passing aqueous liquid through and out of said side opening into contact with said debris; and providing a reduced pressure through said side opening to draw said aqueous liquid and portions of said debris through said side opening into said catheter, said reduced pressure being provided by means of a jet of said aqueous liquid positioned within said catheter adjacent said opening; said jet directing a liquid stream across said opening; and conveying said drawn aqueous liquid and debris portions proximally through said catheter for removal from the body.

18. The method of claim 17 in which said jet of liquid is proximally directed substantially axially with said catheter.

* * * * *